United States Patent [19]

Tzikas

[11] 4,374,989

[45] Feb. 22, 1983

[54] PROCESS FOR THE MANUFACTURE OF DIANTHRAQUINONYL-N,N'-DIHYDROAZINE

[75] Inventor: Athanassios Tzikas, Pratteln, Switzerland

[73] Assignee: Ciba-Geigy AG, Basel, Switzerland

[21] Appl. No.: 293,985

[22] Filed: Aug. 18, 1981

Related U.S. Application Data

[63] Continuation of Ser. No. 149,125, May 8, 1980, abandoned, which is a continuation of Ser. No. 33,406, Apr. 6, 1979, abandoned.

[30] Foreign Application Priority Data

May 8, 1978 [CH] Switzerland ............... 4960/78

[51] Int. Cl.$^3$ .............................................. C09B 5/48
[52] U.S. Cl. .................................................... 544/339
[58] Field of Search ........................................ 544/339

[56] References Cited

U.S. PATENT DOCUMENTS

| | | | |
|---|---|---|---|
| 3,242,182 | 3/1966 | Dien ................................... | 544/339 |
| 3,268,532 | 8/1966 | Zerweck et al. .................... | 544/339 |
| 4,016,182 | 4/1977 | Buecheler ........................... | 260/372 |

OTHER PUBLICATIONS

Mosley, Chem. Ind. (London), (1959), pp. 1348–1349.

Primary Examiner—Paul M. Coughlan, Jr.
Attorney, Agent, or Firm—Wenderoth, Lind & Ponack

[57] ABSTRACT

A process for the manufacture of dianthraquinonyl-N,N'-dihydroazine, which comprises reacting 1-nitroanthraquinone in mixtures of water, alcohols and alkali metal hydroxides at elevated temperature with hydrazine or hydroxylamine compounds, subsequently removing the alcoholic constituents from the reaction mixture, adding dimethyl sulfoxide, and, if desired, further amounts of alkali metal hydroxides, and bringing the reaction to completion at elevated temperature.

11 Claims, No Drawings

PROCESS FOR THE MANUFACTURE OF DIANTHRAQUINONYL-N,N'-DIHYDROAZINE

This application is a continuation of application Ser. No. 149,125, filed May 8, 1980, which application is in turn a continuation of application Ser. No. 33,406, filed Apr. 6, 1979 (both now abandoned).

The present invention provides a process for the manufacture of dianthraquinonyl-N,N'-dihydroazine, which comprises reacting 1-nitroanthraquinone in mixtures of water, alcohols and alkali metal hydroxides at elevated temperature with hydrazine or hydroxylamine compounds, subsequently removing the alcoholic constituents from the reaction mixture, adding dimethyl sulfoxide and, if desired, further amounts of alkali metal hydroxides, and bringing the reaction to completion at elevated temperature.

The reaction of 1-nitroanthraquinone with hydrazine or hydroxylamine compounds is advantageously carried out above room temperature. The reaction temperature can vary within a wide range compatible with the reactants and is preferably between room temperature and the boiling temperature of the reaction mixture. In particular, the reaction of 1-nitroanthraquinone with hydrazine or hydroxylamine compounds is carried out at the boiling temperature of the reaction mixture with reflux cooling. The subsequent removal of the alcoholic constituents from the reaction mixture can be accomplished by known methods, for example by distillation (azeotropic distillation) or, if desired, by extraction. The alcoholic constituents are removed from the reaction mixture preferably by distillation. After addition of dimethyl sulfoxide and, if desired, further amounts of alkali metal hydroxides, the reaction is brought to completion, likewise at elevated temperature. Reaction temperatures between 80° and 140° are normally chosen. Preferably, the reaction is brought to completion at 120° to 125° C. In the final stage of the process, it is advantageous to introduce air into the reaction mixture while heating the latter.

Suitable alkali metal hydroxides are in particular sodium and potassium hydroxide or also mixtures of both. Examples of suitable alcohols are: methanol, ethanol, propanol, isopropanol, n-butanol, benzyl alcohol. Several alcohols can also be used simultaneously in the reaction mixture. The ratio of water to alcohols can vary; preferably equal parts of water and alcohol are employed. In addition, it is preferable to use about equal parts of alkali metal hydroxide and 1-nitroanthraquinone and, based on the amount of this latter, about twice the molar amount of hydrazine or hydroxylamine compound.

A preferred embodiment of the process of this invention consists in carrying out the reaction of 1-nitroanthraquinone with hydrazine or hydroxylamine compounds in mixtures of water, methanol or ethanol and potassium hydroxide.

After removal of the alcoholic constituents from the reaction mixture, it is advantageous to add further amounts of alkali metal hydroxides to the reaction mixture. Preferably, the amount of alkali metal hydroxides added is two to three times greater than the amount added initially. The amount of dimethyl sulfoxide employed is preferably about as great as the amount of water and alcohol initially used.

Examples of hydrazine and hydroxylamine compounds are: hydrazine, hydrazine hydrate, methyl hydrazine, ethyl hydrazine, phenyl hydrazine, hydrazinium chloride, hydrazinium dichloride, hydrazinium sulfate, hydrazinium bromide, benzenesulfonyl hydrazide, hydroxylamine, hydroxylamine hydrochloride, hydroxylammonium sulfate, hydroxylaminesulfonic acid. Preferably, hydrazine or hydroxylamine hydrochloride is used.

The reaction products can be isolated from the reaction mixture in known manner. For example, the reaction mixture is cooled to room temperature, then diluted with water, partially neutralised with a mineral acid, and filtered. The filter cake is washed with hot water and then dried.

The reaction product, dianthraquinonyl-N,N'-dihydroazine (indanthrone, C.I. Vat Blue, C.I. No. 69800), is a valuable vat dye. It has the formula

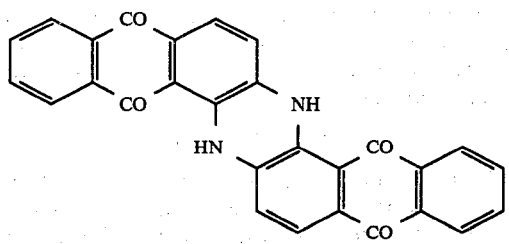

The invention is illustrated by the following Examples, in which the parts and percentages are by weight unless otherwise indicated. The relationship of parts by weight to parts by volume is the same as that of grams to milliliters.

EXAMPLE 1

25.3 parts of 1-nitroanthraquinone are suspended at room temperature in 80 parts of methanol. Then 90 parts of water, 26 parts of solid potassium hydroxide and 8 parts of hydrazine hydrate are added. The suspension is refluxed for 3 hours and the methanol is then distilled off. Then 64 parts of solid potassium hydroxide followed by 70 parts of dimethyl sulfoxide are added cautiously to the suspension. The suspension is heated to 120°–125° C. and kept for 1½ hours at this temperature. The reaction mixture is subsequently kept for a further 3 hours at 120°–125° C., during which time air is introduced. The reaction mixture is then cooled to room temperature, poured into about 2 liters of water and partially neutralised with 300 ml of 4 N hydrochloric acid (pH 9 to 10). The reaction mixture is then filtered. The filter cake is freed from salt and by-products by washing it with hot water, and dried at 70°–80° C. Yield: 20.3 parts (91.8% of theory).

EXAMPLE 2

The same end product is obtained in a yield of 20 parts by repeating the procedure of Example 1 using ethanol instead of methanol.

EXAMPLE 3

The same end product is obtained in a yield of 20.2 parts by repeating the procedure of Example 1 using 10 parts of hydroxylamine hydrochloride instead of 8 parts of hydrazine hydrate.

EXAMPLE 4

The same end product is obtained in a yield of 20 parts by repeating the procedure of Example 1 using ethanol instead of methanol and 10 parts of hydroxylamine hydrochloride instead of 8 parts of hydrazine hydrate.

EXAMPLE 5

The same end product is obtained in a yield of 20 parts by repeating the procedure of Example 1 using 28 parts of hydrazinium sulfate instead of 8 parts of hydrazine hydrate.

EXAMPLE 6

The same end product is obtained in a yield of 20.1 parts by repeating the procedure of Example 1 using 15 parts of hydrazinium chloride instead of 8 parts of hydrazine hydrate.

EXAMPLE 7

The same end product is obtained in a yield of 20.2 parts by repeating the procedure of Example 1 using 23 parts of hydrazinium dichloride instead of 8 parts of hydrazine hydrate.

EXAMPLE 8

The same end product is obtained in a yield of 20 parts by repeating the procedure of Example 1 using 15 parts of hydroxylammonium sulfate instead of 8 parts of hydrazine hydrate.

EXAMPLE 9

The same end product is obtained in a yield of 20.2 parts by repeating the procedure of Example 1 using isopropanol instead of methanol.

EXAMPLE 10

The same end product is obtained in a yield of 20 parts by repeating the procedure of Example 1 using propanol instead of methanol.

EXAMPLE 11

25.3 parts of 1-nitroanthraquinone are suspended at room temperature in 150 parts of methanol. Then 15 parts of solid potassium hydroxide and 8 parts of hydrazine hydrate are added. The suspension is refluxed for 3 hours and the methanol is then distilled off. Then 90 ml of water, 75 parts of solid potassium hydroxide followed by 70 parts of dimethyl sulfoxide are added cautiously to the reaction mixture. The suspension is heated to 120°–125° C. and kept for 1½ hours at this temperature. The reaction mixture is subsequently kept for a further 3 hours at 120°–125° C., during which time air is introduced. The reaction mixture is then cooled to room temperature and poured into about 1 liter of water. The reaction mixture is then filtered. The filter cake is freed from salt and by-products by washing it with hot water, and dried at 70°–80° C. Yield: 20 parts (91.5% of theory).

EXAMPLE 12

The same end product is obtained in a yield of 20 parts by repeating the procedure of Example 11 using ethanol instead of methanol.

EXAMPLE 13

The same end product is obtained in a yield of 20.2 parts by repeating the procedure of Example 11 using isopropanol instead of methanol.

EXAMPLE 14

The same end product is obtained in a yield of 20 parts by repeating the procedure of Example 11 using propanol instead of methanol.

EXAMPLE 15

25.3 parts of 1-nitroanthraquinone are suspended at room temperature in 160 parts of water. Then 26 parts of solid potassium hydroxide and 8 parts of hydrazine hydrate are added. The suspension is refluxed for 3 hours and 70 ml of water are then distilled off. Then 64 parts of solid potassium hydroxide followed by 70 parts of dimethyl sulfoxide are added cautiously to the suspension. The suspension is heated to 120°–125° C. and kept for 1½ hours at this temperature. The reaction mixture is subsequently kept for a further 3 hours at 120°–125° C., during which time an oxygen/nitrogen mixture with 8% by volume of oxygen is introduced. The reaction mixture is then cooled to room temperature and poured into about 1 liter of water. The reaction mixture is then filtered. The filter cake is freed from salt and by-products by washing it with hot water, and dried at 70°–80° C. Yield: 20 parts (91.5% of theory).

What is claimed is:

1. A one-batch process for the manufacture of dianthraquinonyl-N,N'-dihydroazine, which comprises reacting 1-nitroanthraquinone in a mixture of (a) water or a mixture of water and at least one alcohol and (b) an alkali metal hydroxide or a mixture of alkali metal hydroxides at a temperature of between room temperature and the boiling temperature of the reaction mixture with hydrazine, hydrazine hydrate, methyl hydrazine, ethyl hydrazine, phenyl hydrazine, hydrazinium chloride, hydrazinium dichloride, hydrazinium sulfate, hydrazinium bromide, benzenesulfonyl hydrazine, hydroxylamine, hydroxylamine hydrochloride, hydroxylammonium sulfate or hydroxylamine sulfonic acid, subsequently removing any alcoholic constituents present from the reaction mixture, adding to the reaction mixture dimethyl sulfoxide or dimethyl sulfoxide and a further amount of alkali metal hydroxide, and bringing the reaction to completion at a temperature between 80° and 140° C.

2. A process according to claim 1, wherein the reaction of 1-nitroanthraquinone with hydrazine or hydroxylamine compound as defined in claim 1 is carried out at the boiling temperature of the reaction mixture with reflux cooling.

3. A process according to either of claim 1 or claim 2, wherein any alcoholic constituents present are removed from the reaction mixture by distillation.

4. A process according to either of claim 1 or claim 2, wherein the reaction is brought to completion in the temperature range of between 120° to 125° C.

5. A process according to either of claim 1 or claim 2, wherein the reaction is brought to completion while introducing air.

6. A process according to either of claim 1 or claim 2, wherein about equal amounts of water and alcohol are used.

7. A process according to either of claim 1 or claim 2, wherein there are used about equal parts of alkali metal hydroxide and 1-nitroanthraquinone, and, based on the 1-nitroanthraquinone, about twice the molar amount of the hydrazine or hydroxylamine compound as defined in claim 1.

8. A process according to either of claim 1 or claim 2, wherein the reaction of 1-nitroanthraquinone with hydrazine or hydroxylamine compound as defined in claim 1 is carried out in a mixture of water, methanol or ethanol and potassium hydroxide.

9. A process according to either of claim 1 or claim 2, wherein two to three times the initial amount of alkali metal hydroxide is added after removal of any alcoholic constituents present from the reaction mixture.

10. A process according to either of claim 1 or claim 2, wherein dimethyl sulfoxide is employed in an amount about as great as the amount of water and alcohol initially used.

11. A process according to either of claim 1 or claim 2, wherein hydrazine hydrate or hydroxylamine hydrochloride is used.

* * * * *